United States Patent [19]
Guibert et al.

[11] Patent Number: 5,374,284
[45] Date of Patent: Dec. 20, 1994

[54] POWER CONTROL UNIT FOR THERMOTHERAPY APPLICATOR

[76] Inventors: Raul Guibert; Bettina Guibert, both of 750 S. Bundy Dr., Apt. 101, Brentwood, Calif. 90049

[21] Appl. No.: 188,940

[22] Filed: Jan. 31, 1994

Related U.S. Application Data

[63] Continuation-in-part of Ser. No. 26,756, Mar. 5, 1993, Pat. No. 5,315,994.

[51] Int. Cl.$^5$ ............................................. A61F 7/00
[52] U.S. Cl. .................................................. 607/96
[58] Field of Search ........................................ 607/96

[56] References Cited

U.S. PATENT DOCUMENTS

| | | | |
|---|---|---|---|
| 3,207,159 | 9/1965 | Tateisi | 607/96 |
| 4,585,002 | 4/1986 | Kissin | 607/96 |
| 5,107,832 | 4/1992 | Guibert et al. | 607/96 |

*Primary Examiner*—William H. Grieb
*Attorney, Agent, or Firm*—Michael Ebert

[57] ABSTRACT

A power control unit for a thermotherapy applicator adapted to direct toward a localized skin area of a patient overlying a problem region, a stream of hot air whose temperature cyclically alternates between a base level above ambient to a peak level above base to produce a pulsatory heat wave which promotes the transfer of heat to the problem region to raise it to an elevated temperature. The applicator includes a fan driven by a d-c motor that blows air through an a-c powered heater coil to produce an air stream whose temperature depends on the velocity of air blown through the coil; the higher the velocity, the lower this temperature. The velocity is a function of the level of d-c voltage applied to the motor by a rectifier connected to a voltage-divider tap on the coil. The power control unit applies a-c power to the heater coil and acts to cyclically alternate the level of d-c voltage applied to the motor from a level corresponding to its rated voltage to a reduced level whereby the resultant air velocity of the air stream alternates from a high velocity to a low velocity to produce the pulsatory heat wave.

15 Claims, 2 Drawing Sheets

POWER CONTROL UNIT FOR THERMOTHERAPY APPLICATOR

RELATED APPLICATION

This application is a continuation-in-part of our pending application Ser. No. 08/026,756, filed Mar. 5, 1993 entitled "Combined Thermotherapy and Electrotherapy Technique," now U.S. Pat. No. 5,315,994, issued May 31, 1994.

BACKGROUND OF THE INVENTION

1. Field of Invention

This invention relates generally to thermotherapy applicators adapted to direct a stream of hot air toward a localized skin surface of a patient overlying a problem region; the air stream exhibiting a pulsatory heat wave pattern which promotes the transfer of heat to the problem region, and more particularly to an improved control unit for such applicators.

2. Status of Prior Art

Medical practitioners since ancient times have known that the application of heat to the body is useful in the relief of muscle soreness and various aches and pains, as well as in the treatment of certain pathological conditions. Thus the use of heat for the treatment of arthritis and other abnormalities is now commonplace. Hot water bottles and electrical heating pads are in widespread use, not merely to provide warmth, but also to afford a degree of relief or therapy for various conditions. In applying heat to the surface of the body, one may do so by convection, by direct contact with a body to be warmed; that is, by conduction, or by radiating energy into the body.

Difficulty has heretofore been experienced in effectively applying heat which is electrically or otherwise generated to a patient. When transferring heat inwardly through living tissue to a problem region underlying the skin, if the heat applied to the skin surface is within a tolerable temperature range, then not enough heat energy is transferred to this site to afford beneficial effects.

In conventional heat applicators, the heat is applied continuously to the skin area overlying the problem region. This imposes strict limits on the acceptable temperature level. Thus if one seeks to have the heat penetrate more deeply into the body, the temperature at the surface area must be raised to promote more rapid heat transfer, for the higher the differential between the internal and external temperatures, the greater the rate of transfer. But a point is then quickly reached at which the patient is made uncomfortable, for one can only tolerate continuously applied heat when its temperature level is not excessively above body temperature.

The temperature sensitivity threshold for a given patient is that temperature level of the heating medium to which the patient is continuously exposed, above which the patient experiences serious discomfort.

Because continuous heat therapy techniques, to be completely safe, must operate at a relatively low temperature level not much higher than the sensitivity threshold, they are of limited effectiveness in the treatment of backache and other painful conditions that are relieved by heat.

The Guibert U.S. Pat. No. 4,667,658 discloses a technique for applying therapeutic heat to a localized skin surface overlying a problem region. In this technique, the skin surface is exposed to a heating medium whose temperature is at a base level that is well above ambient but no higher than the temperature sensitivity threshold, the temperature of the medium being periodically raised above base level to create high heat energy pulses whose peak temperatures are much higher than the threshold.

The duty cycle of these pulses is such as to allow for internal heat transfer to take place in the problem region below the exposed area of the patient in the intervals between pulses to an extent preventing an excessive rise in temperature at the skin surface whereby the patient gains the benefit of high heat energy treatment without discomfort or injury.

To carry out this technique, the Guibert '658 patent discloses a system in which a motor-driven centrifugal air blower operated at a constant speed draws air from the atmosphere at ambient temperature and blows this air through an applicator which can be oriented to direct the hot air stream to impinge on the localized skin surface of the patient being treated, the hot air then being discharged into the atmosphere.

Mounted at the inlet of the blower motor is an electrical heater coil which acts to heat the air drawn into the blower. An electronic controller is interposed between the heater element and a high voltage supply to energize the heater with a relatively low voltage to establish the base temperature level in the pulsatory heating pattern to which the patient is subjected. The electronic controller is periodically bypassed by means of a repeat cycle timer, whereby the high voltage from the supply is then directly applied to the heater element to raise the air temperature well above the base level to create high energy pulses whose peaks are much higher than the threshold.

The difficulty with the Guibert '658 arrangement in which the voltage applied to the heater is modulated, is that because of thermal inertia, clearly defined heat peak pulses are not produced.

The Guibert et al. U.S. Pat. No. 5,190,031 discloses a thermotherapy applicator in which a fan driven by a d-c motor blows air through an a-c powered heater coil to produce a stream of hot air that is directed toward a localized skin surface, the air stream exhibiting a pulsatory heat wave pattern in which the temperature cyclically alternates from a base to a peak level.

In the Guibert et al. '031 applicator, the temperature to which the air is raised depends on the velocity of air blown by the fan through the heater coil, the greater the air velocity, the lower the temperature level. An electronic control system is associated with the fan motor to periodically change the fan velocity from a predetermined high value at which the resultant temperature level of the air stream is at a base level above ambient but no higher than sensitivity threshold of the patient being treated, to a predetermined low velocity value at which the resultant temperature level is raised above the base level to create high temperature heat pulses whose peaks are well above the sensitivity threshold.

To produce periodic changes in air velocity, the d-c motor driving the fan is energized by a d-c power supply connected to a 120 VAC power line, the supply including a step-down transformer whose output is rectified to field a low voltage d-c output corresponding to the rated voltage of the motor (12 VDC).

Connected in series between the output of the rectifier and the input to the motor is a resistor which drops the voltage applied to the d-c motor to a level somewhat below its rated value. This resistor is periodically short-circuited by a repeat cycle timer so that in each timed cycle of operation, the voltage applied to the motor input alternates from its rated value (12 VDC) to a reduced value (8 VDC), thereby causing the air velocity to alternate cyclically from a high velocity to a low velocity.

It is important to understand the relationship between the velocity of air passing through the heater and the amount of heat imparted to this air by the heater. When the fan is operating at high speed, as a consequence of which the air passes quickly through the heater coil, then the amount of heat imparted to the air in the course of its transit through the coil will be small, resulting in a relatively low rise in air stream temperature. When, however, the fan is operating at low speed and the air then passes slowly through the heater coil, then more heat will be imparted to the air in the course of its transit through the heater coil. This will result in a relatively high rise in air stream temperature.

In the Guibert et al '031 applicator, when the motor operates at its rated voltage, the fan velocity is then high and the air is heated to a base level above ambient temperature but somewhat below the sensitivity threshold of the patient. When the motor operates at below its rated voltage and the fan velocity is low, the air is then heated to an elevated peak temperature level well above the sensitivity threshold.

The difficulty experienced with the applicator arrangement disclosed in the Guibert et al. '031 patent is that it is relatively inflexible and cannot be readily accommodated to the needs of a particular patient. No two patients have the same temperature sensitivity threshold, and a peak temperature level set for one patient may be too high or too low for another.

SUMMARY OF INVENTION

In view of the foregoing, the main object of this invention is to provide an improved power control unit for a thermal applicator adapted to direct a stream of hot air toward a localized skin surface of a patient, the air stream exhibiting a pulsatory heat wave pattern that promotes the transfer of heat from the skin surface to a problem region underlying this surface.

More particularly, an object of this invention is to provide a power control unit which makes it possible to vary the a-c power supplied to the heater coil of the applicator as well as the d-c voltage supplied to the d-c motor driving the fan blowing air through the heater coil to produce a pulsatory heat wave pattern whose base and peak temperature levels are appropriate to the needs of the patient being treated.

A significant advantage of the invention is that d-c power for energizing the d-c motor is not obtained from a separate power supply having a step-down transformer, but from a rectifier connected to a tap on the a-c powered heater coil which also acts as a voltage divider, so that for a given high a-c voltage applied across the coil, the value of a-c yielded at the tap depends on the tap position along the coil.

Yet another object of the invention is to provide an improved power control unit for an applicator producing a hot air stream whose temperature cyclically alternates between a base and a peak level, the applicator including temperature-sensitive safety switches.

Briefly stated, these objects are attained in a power control unit for a thermotherapy applicator adapted to direct toward a localized skin area of a patient overlying a problem region, a stream of hot air whose temperature cyclically alternates between a base level above ambient to a peak level above base to produce a pulsatory heat wave which promotes the transfer of heat to the problem region to raise it to an elevated temperature.

The applicator includes a fan driven by a d-c motor that blows air through an a-c power heater coil to produce an air stream whose temperature depends on the velocity of air blown through the coil; the higher the velocity, the lower this temperature. The velocity is a function of the level of d-c voltage applied to the motor by a rectifier connected to a voltage-divider tap on the coil. The power control unit applies a-c power to the heater coil and acts to cyclically alternate the level of d-c voltage applied to the motor from a level corresponding to its rated voltage to a reduced level whereby the resultant air velocity of the air stream alternates from a high velocity to a low velocity to produce the pulsatory heat wave.

BRIEF DESCRIPTION OF DRAWINGS

For a better understanding of the invention, as well as other features thereof, reference is made to the following detailed description and the accompanying drawings wherein.

DETAILED DESCRIPTION OF INVENTION

General Description

Figure 1:
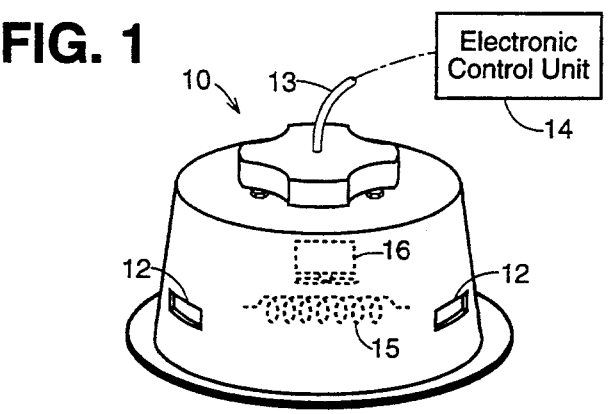
FIG. 1 illustrates a thermotherapy applicator and a power control unit therefor.

Referring now to FIG. 1, there is shown an applicator according to the invention, the applicator including a dome-shaped casing 10 molded of high-strength, fire-retardant, synthetic plastic material having electrical insulating properties. Suitable for this purpose is polycarbonate. Casing dome 10 has an open base surrounded by a circular flange 11. In practice, fitted onto this flange is an annular ring of elastomeric material which acts as a protective cushion when the applicator is applied to the skin of the patient being treated. Formed in the wall of the dome and adjacent flange 11 is a circular series of air-inlet ports 12 of predetermined size. The applicator is coupled by a flexible cable 13 to an electrical power control unit 14 which supplies operating power to the electrical heater 15 and to the fan motor 16 included in the applicator.

The manner in which the applicator 10 operates is disclosed in greater detail in the Guibert et al. U.S. Pat. No. 5,190,031 whose disclosure is incorporated herein by reference.

Electronic control unit 14 functions to apply AC operating power to electric heater coil 15 and to control this power so that the temperature of the air applied to a patient being treated can be tolerated by the patient, bearing in mind that no two patients have exactly the same threshold sensitivity and that some patients are rendered uncomfortable at temperatures which are acceptable to others. In practice, therefore, it is desirable that the control unit be capable of being adjusted to effect temperature changes in small increments.

While heater coil 15 is being energized, the DC fan motor 16 has an operating voltage applied thereto which changes periodically from its rated voltage to a lower voltage level. Thus if the rated voltage for the fan motor is 12 volts DC, at which voltage the fan operates at high velocity, and the voltage applied to the motor changes periodically from 12 volts to 8 volts DC, then the fan velocity will go periodically from high to low.

An applicator in accordance with the invention functions to carry out a thermotherapy technique in which heat energy is applied to a localized skin surface area of a patient overlying a problem region by an air stream whose temperature in the intervals when the velocity of the air stream is high is at a substantially constant base level well above ambient but somewhat below the sensitivity threshold of the patient. In the intervals in which the velocity of the air stream is low, its temperature is then elevated to reach a peak level well above the sensitivity threshold. Thus if the temperature were maintained at this peak level for, say, a minute or more, though it would then act to promote rapid heat transfer inwardly to the problem region in the body, it would at the same time cause extreme discomfort and possible injury to the patient.

In order, therefore, to render the applied heat energy tolerable and at the same time bring about a rapid inward heat transfer from the skin area to the problem region, the heat energy in a technique in accordance with the invention is applied in a pulsatory thermal wave pattern.

Figure 2:
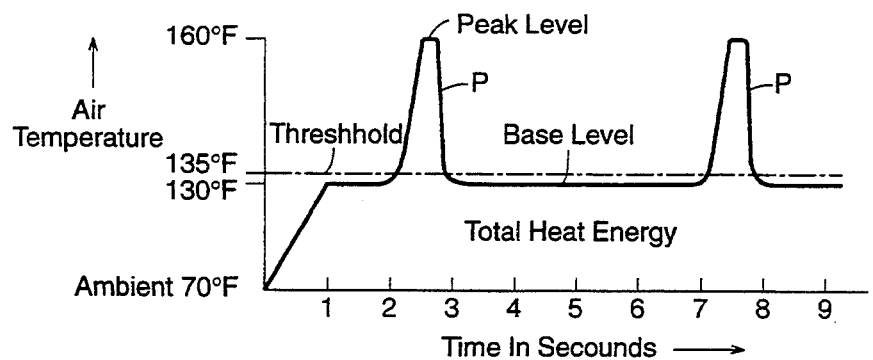
FIG. 2 is a waveform showing the pulsatory heat wave pattern of the air stream produced by the applicator.

This thermal wave pattern is shown graphically in FIG. 2. The air temperature which is drawn from the atmosphere is initially at ambient (i.e., 70° F.). When the velocity of the air as controlled by the fan is high, then the air is heated to a constant base temperature level (i.e., 130° F.) which is well above ambient (70° F.) but somewhat below the temperature sensitivity threshold of the patient (i.e., 135° F.).

In FIG. 2, temperature is plotted against time in one second increments. It will be seen that the temperature of the air stream is periodically raised well above its base level by heat energy pulses to a peak level (i.e., 160° F.), which is much higher than the sensitivity threshold. This rise in temperature takes place when the air velocity, as controlled by the fan, is low.

In the example shown, the duty cycle is such that each pulse P, which has almost a one second duration, is followed by an interval of four seconds in which the flowing air stream is at its base level temperature.

The resultant pulsatory thermal air wave pattern is such that the stream of hot air at the base temperature level is blown toward the localized skin area to impinge thereon. This air stream is periodically raised in temperature to a peak level so that the localized skin area being subjected to treatment is exposed to high temperature heat energy well above the sensitivity threshold for no more than a brief period insufficient to cause discomfort, followed by an interval at the markedly lower base temperature level during which rapid heat transfer takes place through the body tissue toward the problem region. This inward transfer acts to reduce the temperature at the surface to a degree preventing a significant rise thereof above the sensitivity threshold.

A technique in accordance with this invention makes it possible to produce a great rise in the temperature of an internal problem region underlying a limited skin area subjected to the heat without, however, discomfort to the patient or damage to the tissue being heated. Because the internal heat is significantly higher in temperature than that heretofore obtainable without discomfort or damage, the beneficial effects on the problem region are far more pronounced.

The one-second peak temperature interval and the four-second base temperature interval shown in FIG. 2 is by way of example only, for in practice, the duration and temperature levels of the peak and base intervals are adjusted to values appropriate to the condition of the patient being treated.

First Embodiment

Figure 3:
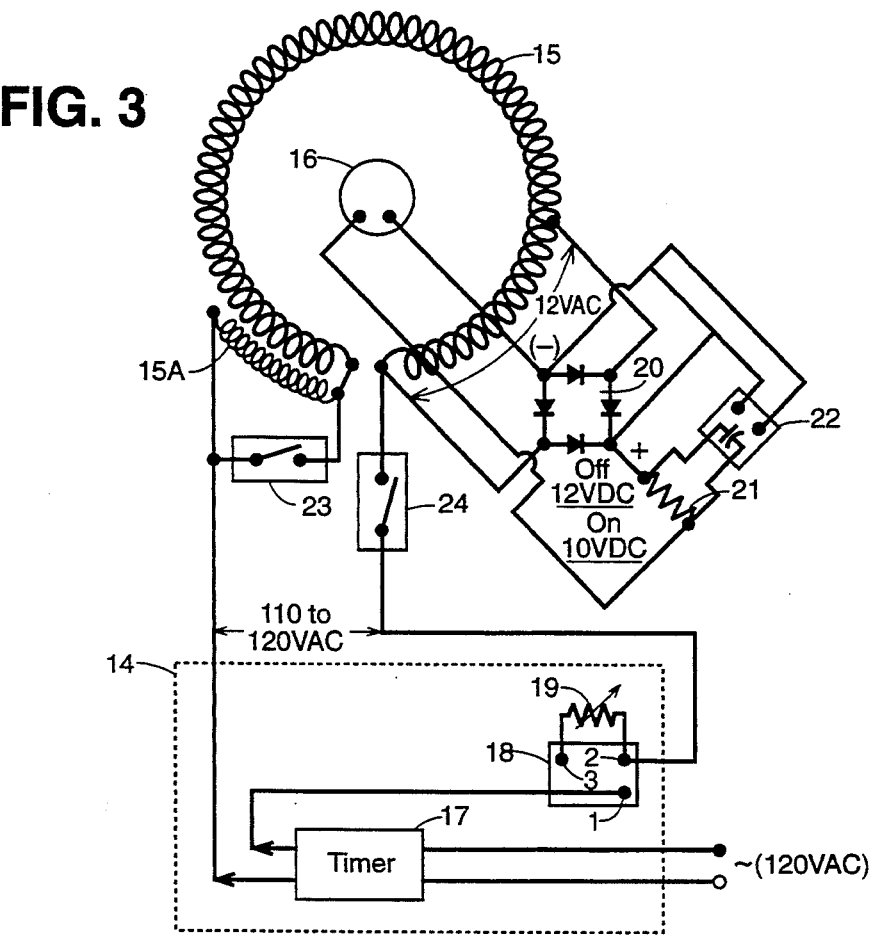
FIG. 3 is a schematic circuit diagram of a first embodiment of an applicator and a power control unit in accordance with the invention.
Figure 4:
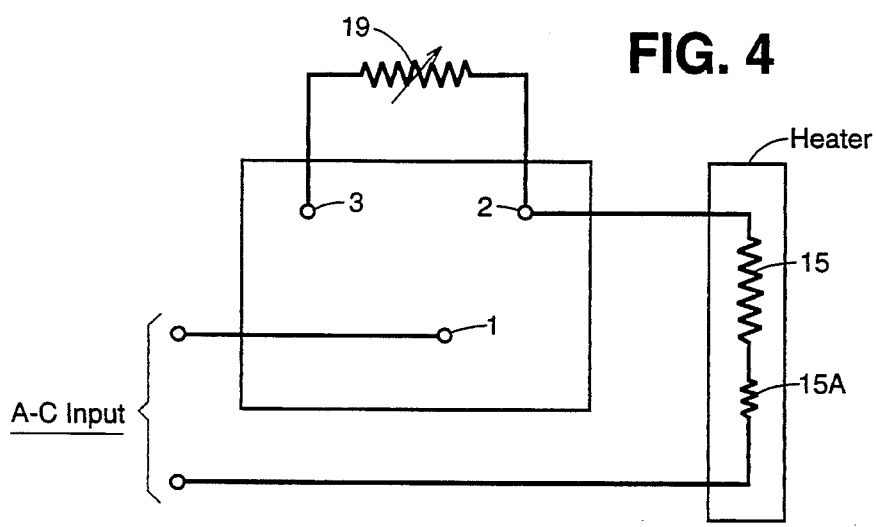
FIG. 4 separately shows the phase-control device included in the power control unit.
Figure 5:
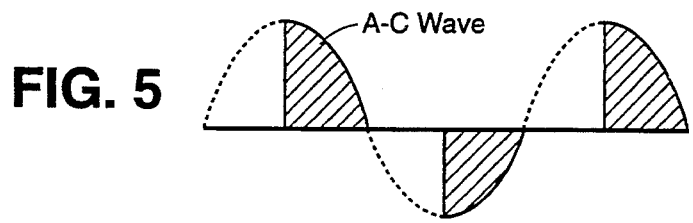
FIG. 5 illustrates the wave form of the phase-control unit.

Referring now to FIG. 3, there is shown schematically the heater coil 15 of the applicator which is in a ring formation as in U.S. Pat. No. 5,190,031. Connected in series with heater coil 15 is an auxiliary heater coil 15A whose function will be later explained. Air is blown through the heater coils 15 and 15A by a d-c fan motor 16.

The control unit 14 for the applicator which is housed in a separate box, includes an adjustable timer 17. Timer 17 which is connected to an a-c power line (120 VAC) applies power through a power control device 18 across the serially-connected heater coils 15 and 15A. Power control device 18 whose adjustment is effected by a potentiometer 19, serves to vary the a-c voltage applied to the heaters in a range such as 100 VAC to 120 VAC. The time period during which the applicator remains operative is controlled by the adjustable electronic clock of timer 17 which, in practice, may have a 1 to 30 minute range. Thus if the patient is to undergo thermotherapy treatment for 15 minutes, the timer is set accordingly.

Power control device 18 is preferably of the phase-control type, such as a solid state PHS Series phase-control devices marketed by SSAC Inc. of Baldwinsville, N.Y. Phase-control devices are commonly used as a dimmer to change lamp intensity, to vary the speed of a fan or other motor, and to control the temperature of an electric heater.

The manner in which phase-control device 18 operates in the context of the present invention will now be explained the peak temperature level of the pulsatory heat wave, the d-c voltage applied to the fan motor is reduced periodically so that it blows air at a relatively low velocity through the heater coils.

This reduction in d-c voltage is effective by a voltage-dropping resistor 21 interposed between rectifier 20 and the input to d-c fan motor 16. Resistor 21 is periodically shunted by a flip-flop electronic switching device 22 whose d-c operating power is derived from rectifier 20. Each cycle of flip-flop operation produces a negative pulse followed by a positive pulse, the duration of each pulse being adjustable. The negative pulse of the switching device creates an open circuit across resister 21 for say two seconds, so that a reduced voltage of 10 VAC is then applied to motor 16. During the positive pulse of each switching cycle, the resistor is shunted and thereby short-circuited for say six seconds, so that the full 12 VDC from the rectifier 20 is then applied to the motor.

When a reduced d-c voltage is applied to fan motor 16, the resultant air velocity is low and this produces the high temperature peak in the pulsatory heat wave. When the full d-c voltage is applied to motor 16 which corresponds to its rated voltage, then the air velocity is high, thereby producing the base temperature of the pulsatory heat wave.

Because the duty cycle of the flip-flop switching device 22 is adjustable, the operator of the applicator may select any desired pulsatory heat wave pattern, such as one having a one second peak temperature interval and a four second base temperature interval in each cycle of the pulsatory wave.

In practice, the rectifier 20 and the flip-flop solid state switching device 22 may be mounted on a printed circuit board disposed within the casing of the applicator. In this arrangement the power control unit 14 which is connected by cable 13 to applicator 10 contains only timer 17 and phase-control device 18. This unit may also be provided with a master switch and a safety fuse (not shown).

In order to prevent an excessive rise in the average temperature of the pulsatory air stream produced when the blower 16 is in operation, placed within the applicator to sense this temperature is a normally-closed, bi-metallic thermo-switch 23. This switch is connected across auxiliary heater coil 15, so that the coil is then short circuited.

When the average temperature of the pulsatory air stream reaches an unacceptable level, say 140° F., switch 23 then opens and the a-c power is then applied to the series-connected heater coils 15 and 15A whose resistance is higher than that of heater coil 15 alone. As a result, the heat produced by the series-connected heater coils is less than that produced by heater 15 alone whereby the average temperature then falls to an acceptable level below 140° F.

Should fan motor 16 become inoperative for any reason, then no air is blown through the heater coils to extract heat therefrom. As a result, the heat within the applicator will rise to an unacceptable level, say 170° F. and higher. As a safety measure, a normally-closed, bi-metallic thermoswitch 24 is connected in series with heater coil 15. This switch opens to cut off a-c power to coil 15 when the temperature within the applicator reaches 170° F.

FIG. 3 shows the circuit of a single applicator which is energized from a 110 VAC power line, hence heater coil 15 which is formed of nichrome wire has a resistance appropriate to this high a-c voltage. In practice, the power control unit 14 may serve to regulate a pair of applicators adapted to direct streams of hot air having a pulsatory thermal wave pattern toward opposite sides of a limb or other body member of a patient. The patient may be an animal, such as a horse, rather than a human being.

In that case, the heater coils of the two applicators are connected in series to the power control unit 14 to whose input is applied 120 VAC, the heater coil in each applicator being designed in this instance to operate at 60 VAC.

Figure 6:
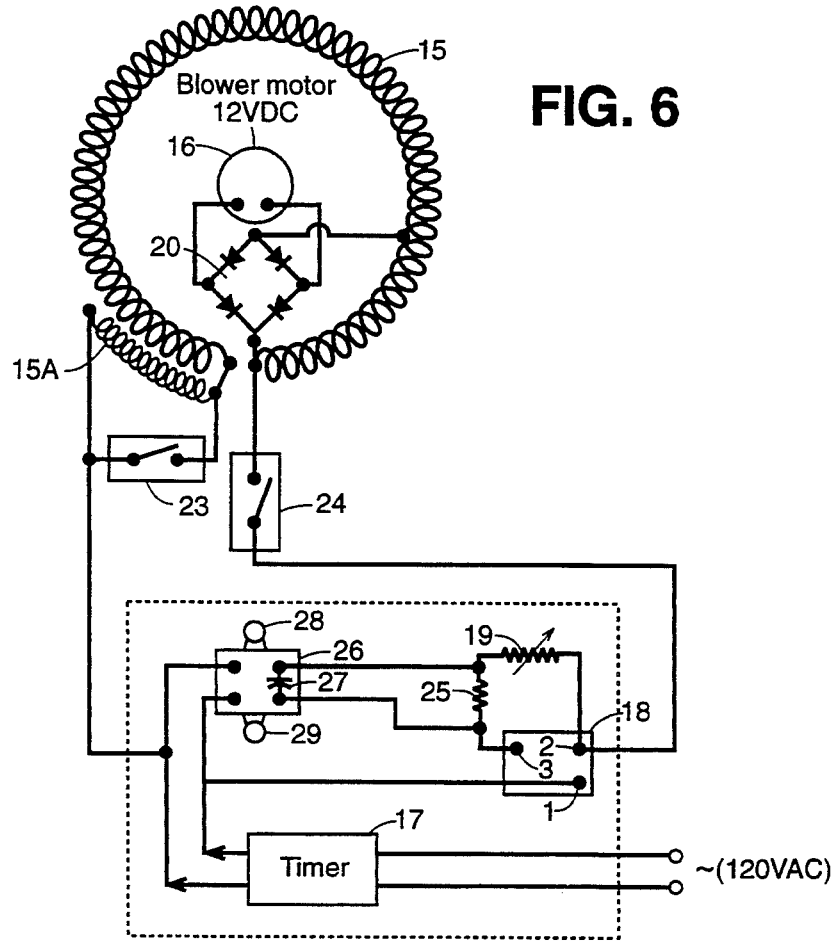
FIG. 6 is a schematic circuit diagram of a second embodiment of the invention.

Second Embodiment:

In this embodiment the applicator, as in the first embodiment, includes as shown in FIG. 6 a main heater coil 15 and an auxiliary heater coil 15A, as well as a d-c motor-driven blower 16 powered by d-c derived from a full wave rectifier 20 whose input is connected between tap T of coil 15 and one end thereof.

But instead of periodically reducing the d-c voltage applied to blower 16 by means of a resistor interposed between the d-c blower motor and rectifier 20, which resistor is periodically short-circuited by a flip-flop switching device, as in the first embodiment, in the second embodiment a periodic reduction in the d-c voltage applied to the motor is effected by periodically reducing the a-c voltage applied to heater coil 15. This reduction in a-c voltage across heater coil 15 which acts as a voltage divider, causes a reduction in a-c voltage at tap T with a consequent reduction in the d-c output of rectifier 20.

In the second embodiment, phase-control unit 18 which adjusts the level of a-c voltage applied to the heater coil 15 includes in addition to potentiometer 19 for effecting this adjustment, a fixed resistor 25 in series with the potentiometer.

Resistor 25 is periodically shorted out by a repeat cycle timed switching device 26. Device 26 is energized by a-c power derived from timer 17 and acts to periodically close a switch 27 shunted across resistor 25. When resistor 25 is shorted out, the a-c voltage yielded by the phase-control device 18 is determined by the setting of potentiometer 19 and lies in the range of 100 VAC to 120 VAC. And since the d-c voltage for the motor is derived from rectifier 20 connected to tap T on heater coil 15, the d-c voltage is also determined by the setting of potentiometer 19. We shall assume the potentiometer 19 is set to apply 120 VAC to heater coil 15 and that the d-c then applied to motor 16 is 12 VDC and corresponds to the rated voltage of the motor.

When resistor 25 in the course of an operating cycle of the repeat cycle timed switching device 26 is not shorted out because switch 27 is now open, then the a-c voltage applied to heater coil 15 is reduced to say 100 VAC and the d-c voltage applied to motor 16 is reduced to 8 VDC.

When the fan motor is powered at its rated a-c voltage, it produces a high velocity air stream flowing through the heater coil, and when it is powered at a reduced d-c voltage, the velocity of the air stream is reduced. The high velocity stream results in the base temperature level of the pulsatory heat wave, and the low velocity stream in the peak level thereof.

In order to be able to adjust the duration of the peak level interval and the duration of the base level interval in each cycle of the heat wave, repeat cycle timed switching device 26 is provided with a potentiometer 28 which controls the duration of the "on" interval in each cycle in which switch 26 is closed to raise the d-c voltage applied to the motor, and a potentiometer 29 which controls the duration of the "off" interval in which switch 27 is open to decrease the d-c voltage applied to the motor. Hence by means of these potentiometers the operator is able to adjust the duration of the peak temperature interval in the pulsatory heat wave and to adjust the base level temperature.

In the first embodiment, the a-c voltage applied to the heater coils remains at a set level during the course of applicator operation, whereas the d-c voltage applied to the fan motor cyclically alternates from a high to a low d-c level. In the second embodiment, the a-c voltage applied to the heater coils also cyclically alternates from a high to a somewhat lower level. But this does not act to pulse the heat produced by the heater coils. The reason for this is that the coils exhibit thermal inertia, and a drop in the a-c applied to the coils for a few seconds in each cycle does not result in a significant reduction in heater temperature.

While there have been shown preferred embodiments of the invention, it is to be understood that many changes may be made therein without departing from the spirit of the invention.

We claim:

1. A thermotherapy applicator and a power control unit therefor comprising:
   A. an a-c operated heater coil;
   B. a d-c fan motor adapted to blow air through the coil to produce a hot air stream to be directed toward a localized area of a patient to be treated, said motor having a rated d-c operating voltage;
   C. an a-c power source applying an a-c voltage across the heater coil to energize same;
   D. a rectifier connected to a voltage-divider tap on the coil to produce a d-c output voltage whose level depends on the a-c voltage at the tap, said d-c output voltage being applied to the motor to energize same; and
   E. means cyclically to alternate said d-c output voltage from a level substantially equal to the rated voltage of the motor to a reduced level whereby in each operating cycle, the velocity of air blown through the coil alternates from a high to a low velocity to produce a hot air stream having a pulsatory heat wave pattern which promotes the transfer of heat in the body of the patient.

2. The combination as set forth in claim 1, in which the voltage of the power line is 120 VAC, the rated voltage of the motor is 12 VDC and the voltage at the tap is about 12 VAC.

3. The combination as set forth in claim 1, in which the pulsatory heat wave pattern in each cycle thereof exhibits a base temperature level above ambient and a peak temperature level above the base level.

4. The combination as set forth in claim 1, in which the heater coil is connected to said a-c power source in series with an auxiliary heater coil shunted by a normally-closed thermoswitch that when the temperature of the air emerging from the heater coil exceeds a predetermined unsafe value, then opens to render the auxiliary coil effective to increase the resistance presented to the power supply and thereby lower the air temperature below said value.

5. The combination as set forth in claim 1, in which a normally-closed thermoswitch is interposed between said heater coil and said power supply, which switch opens when the motor is inoperative and the heater coil temperature then rises to an excessive level because no air is blown therethrough.

6. The combination as set forth in claim 1, in which the rectifier is a four-diode bridge providing full-wave rectification.

7. The combination as set forth in claim 1, in which said means cyclically to alternate said d-c output voltage applied to the motor acts to periodically reduce the a-c voltage supplied by said a-c source to said heater coil whereby the a-c voltage on said tap alternates from a high to a low value.

8. The combination as set forth in claim 1, in which said source includes a phase-control device adapted to adjust the level of a-c voltage applied to said heater coil.

9. The combination as set forth in claim 1, in which said source is connected to an a-c power line through a settable timer to switch off the a-c voltage supplied to said coil after a set time period.

10. A thermotherapy applicator and a control unit therefor comprising:
    A. an a-c operated heater coil;
    B. a d-c fan motor adapted to blow air through the coil to produce a hot air stream to be directed toward a localized area of a patient to be treated; said motor having a rated d-c operating voltage;
    C. an a-c power source to apply an a-c operating voltage to said heater coil derived from an a-c power line;
    D. a rectifier connected to a voltage-divider tap on said coil to produce a d-c output voltage which is applied to said motor;
    E. a resistor interposed between the rectifier and the motor to drop the d-c voltage applied thereto; and
    F. a repeat cycle switching device connected across the resistor to periodically short circuit the resistor whereby in each cycle the output voltage applied to the motor alternates from a voltage substantially equal to the rated voltage to a reduced voltage, thereby causing the air blown through the coil to have a velocity which alternates in each cycle from a high to a low velocity to produce a hot air stream having a pulsatory wave pattern that promotes heat transfer in the body of the patient.

11. The combination as set forth in claim 10, in which the repeat cycle switching device is governed by a flip-flop circuit.

12. A thermotherapy applicator and a power control unit therefor comprising:
    A. an a-c operated heater coil;
    B. a d-c fan motor adapted to blow air through the coil to produce a hot air stream to be directed toward a localized area of a patient to be treated, said motor having a rated operating voltage;
    C. a rectifier connected to a voltage-divider tap on the coil to produce a d-c output voltage which is applied to the motor;
    D. an a-c power source to apply an a-c voltage derived from an a-c power line to the coil, said source being provided with means cyclically to alternate the a-c voltage applied to the coil from a high a-c value to a reduced value whereby the a-c voltage at the tap undergoes a corresponding alternation and the resultant d-c output voltage alternates from a level substantially equal to the rated voltage to a reduced voltage, as a consequence of which the velocity of air blown through the coil by the fan motor alternates in each cycle from a high to a relatively low velocity to produce a hot air stream that exhibits a pulsatory heat wave pattern that promotes the transfer of heat in the body of the patient.

13. The combination as set forth in claim 12, in which said means cyclically to alternate the a-c voltage includes a phase-control device whose output is controlled by a potentiometer in series with a fixed resistor across which is a repeat cycle timing switch that acts to periodically short circuit the resistor whereby the level of a-c voltage yielded by the device alternates from a high value to a reduced value.

14. The combination as set forth in claim 13, in which the repeat cycle timing switch is provided with a first potentiometer to adjust the duration of the interval in which the switch is open, and a second potentiometer to adjust the duration of the interval in which the switch is closed.

15. The combination as set forth in claim 13, in which the source includes a settable timer interposed between the phase-control device and the a-c power line, the timer cutting off power to the device after a pre-set time period.

* * * * *